United States Patent [19]

Bachhuber et al.

[11] Patent Number: 4,588,579

[45] Date of Patent: May 13, 1986

[54] PROCESS FOR THE PRODUCTION OF THIN SECTIONS OF BIOLOGICAL TISSUE

[75] Inventors: Karlheinz Bachhuber, Ulm; Dieter Frösch, Blaustein, both of Fed. Rep. of Germany

[73] Assignee: Rolf Bachhuber, Blaubeuren, Fed. Rep. of Germany

[21] Appl. No.: 541,966

[22] Filed: Oct. 14, 1983

[30] Foreign Application Priority Data

Oct. 19, 1982 [DE] Fed. Rep. of Germany ....... 3238639

[51] Int. Cl.$^4$ .......................... G01N 1/06; A01N 1/00; A01N 1/02; A01N 3/00

[52] U.S. Cl. ........................................... 424/3; 435/1; 427/4

[58] Field of Search ..................... 424/3; 435/1; 427/4

[56] References Cited

U.S. PATENT DOCUMENTS

| | | | |
|---|---|---|---|
| 3,257,279 | 6/1966 | Schain | 424/3 |
| 3,527,863 | 9/1970 | Weichselbaum | 424/3 |
| 3,624,197 | 11/1971 | Schain | 424/3 |
| 3,961,097 | 6/1976 | Gravlee, Jr. | 424/3 X |
| 4,334,844 | 6/1982 | Tanaka | 427/4 X |
| 4,497,792 | 2/1985 | Gindler | 424/3 |

OTHER PUBLICATIONS

The Condensed Chemical Dictionary, 8th ed., VMR Co., N.Y., 1971, pp. 48, 548 & 915.

Primary Examiner—David M. Naff
Attorney, Agent, or Firm—Frost & Jacobs

[57] ABSTRACT

The present invention provides a process for the production of thin sections of biological tissue, especially for transmission electron microscopy. In the process a fixed tissue sample to be investigated is dehydrated by infiltration of a hardenable medium miscible with water and subsequently embedded in casting resin, whereafter thin sections are cut from the cast body resulting after hardening of the casting resin. Infiltration is carried out by warming the fixed tissue sample in a mixture of formaldehyde, melamine and water. During warming, the mixture forms water soluble monomeric methylolmelamines which infiltrate the tissue and undergo polycondensation to form water-insoluble polymeric methylolmelamine condensates in the tissue. The casting resin is preferably a melamine resin, and the resin is preferably prepared using a methylolmelamine ether solution containing polyethylene glycol.

10 Claims, No Drawings

PROCESS FOR THE PRODUCTION OF THIN SECTIONS OF BIOLOGICAL TISSUE

The present invention is concerned with a process for the production of thin sections of biological tissue, especially for transmission electron microscopy, in which a fixed tissue sample to be investigated is dehydrated by infiltration of a hardenable medium miscible with water and is subsequently embedded in casting resin, whereafter thin sections are cut from the cast bodies resulting after the hardening of the casting resin. The present invention is also concerned with a hardenable infiltration agent for biological tissue, especially for the preparation of tissue samples for thin layer electron microscopy, which can be used for the carrying out of the process according to the present invention.

For transmission electron microscopy, ultrathin sections of the structures to be investigated are necessary. In the case of biological material and especially of tissue of any desired origin, this can only be cut up into samples with a thickness of 2–100 nm, without destruction of the tissue and cell structures, when the free water contained in the tissue is replaced by a non-volatile, readily sectile resin. Fundamental prerequisites which such a resin must fulfil are ready availability and handling, uniform reproducability, solubility in the dehydration agent used, low viscosity in the nonhardened state, uniform, isotropic polymerisation, lowest possible volume change in the case of the polymerisation, good cuttability, stability in the electron beam and, last but not least, the lowest possible impairment of the structure of the biological material.

Large numbers of processes of the initially mentioned kind are known (cf. "Principles and Techniques of Electron Microscopy" by M. A. Hayat, pub. Van Nostrand Resinhold, New York, 1970). Before the exchange of the water by a non-volatile, readily sectile resin, the tissue sample to be investigated is fixed by known methods, which are also described in the mentioned publication. The exchange of the water by organic solvents is called "dehydration" and the subsequent penetration of the resin into the sample is called "infiltration". The hardenable medium used for the infiltration is called an infiltration agent but often also, but not quite correctly, is called an "embedding material" or "embedding mass". However, the water exchange taking place by infiltration into the tissue is to be sharply differentiated from the embedding of the already infiltrated tissue sample into a casting resin, which is known and suitable for this purpose, for the production of a cast body, from which thin sections can then be cut out, in the case of which the "casting resin disc" functions as an object carrier of the thin tissue section contained therein.

As already mentioned, as infiltration medium use has previously always been made of hardenable resins, i.e. substances which have already been polymerised to macromolecules but not yet hardened by cross-linking and which are soluble to a sufficient extent in an appropriate solvent adapted to the constitution and the functional groups of the resin.

The epoxide resins initially used for the infiltration had the disadvantage that, because these resins are water-soluble, before the infiltration of the resin a dehydration of the tissue with organic solvents, usually acetone or ethanol, is abolsutely essential. However, the exchange of the water by acetone or ethanol leads to the extraction of lipids and, to a considerable extent, to the denaturing of proteins. Therefore, the finally obtained electron-optical picture no longer gives, in sufficient approximation, the original state of the tissue and cell structures.

Therefore, attempts have already been made to use water-soluble resins or polymers, especially polyethylene glycol and arcylates and methacrylates miscible with water as infiltration agents. These resins do not require any previous dehydration of the tissue with organic solvents but have the disadvantage that they themselves extract neutral lipids and phospholipids to a considerable extent and thus act as an organic solvent.

Finally, it has also already been suggested (cf. loc. cit., pp. 178–179) to use urea-formaldehyde adducts, which are water-soluble or miscible with water, as aqueous infiltration agents. Urea and formaldehyde react in alkaline solution with the formation of polymeric hardenable resins which are absolutely insoluble in almost all solvents, including water. However, if the polycondensation reaction is artificially interrupted in an appropriate manner, water-soluble polymeric urea-formaldehyde resins result which can be used as aqueous infiltration agents. Although these resins have the advantage of not or only scarcely reducing the lipid content of the tissue, they cannot be used in practice because, during drying and hardening, i.e. during the completion of the interrupted polycondensation and of the cross-linking, which take place after the water exchange within the tissue, they shrink to a considerable extent, cracks and fissures being formed which, by deflection of the electron beam on the boundary surfaces, by anisotropic properties in the fissure region, by density gradients and the like, disturb and falsify the electron-optical picture.

It is an object of the present invention to provide a process of the initially mentioned kind and an infiltration agent suitable for the carrying out of such a process, with which it is possible also to omit the preliminary insertion of an exchange of the water contained in the tissue by organic solvents and to avoid the disadvantages of the urea-formaldehyde method, i.e. to provide a process and an infiltration agent with the help of which there can be produced crack-free, non-brittle thin sections with the greatest possible maintenance of the original tissue structure, without dissolving out lipids and without denaturing proteins.

Thus, according to the present invention, there is provided a process for the production of thin sections of biological tissue, especially for transmission electron microscopy, in which a fixed tissue sample to be investigated is dehydrated by infiltration of a hardenable medium miscible with water and subsequently embedded in casting resin, whereafter thin sections are cut from the cast body resulting after hardening of the casting resin, wherein a fixed tissue sample is warmed in a mixture of formaldehyde, melamine and water, the tissue sample being simultaneously infiltrated with the resulting aqueous solution.

If desired, the mixture of formaldehyde, melamine and water used can also contain an agent for the adjustment of the pH value.

Melamine is comparatively poorly soluble in water: the solubility L is, at temperature T (in °C.): log $L = -1642/T + 5.101$ (g./100 g. water). Formaldehyde is a gas which is readily soluble in water. According to the present invention, for reasons of practicability, the formaldehyde is preferably used as a dilute aqueous solution (formalin) or in crystalline form (paraformaldehyde), which dissolves slowly in cold water but dissolves easily in hot water and in dilute aqueous sodium hydroxide solution.

If a mixture of solid paraformaldehyde or of formalin solution, solid melamine and water is warmed, then a pure suspension of solid melamine in formalin solution is first obtained. However, the melamine gradually dissolves in the formalin solution and reacts with the formaldehyde with the formation of methylolmelamines. Depending upon the stoichiometric amounts of formaldehyde and melamine employed and depending upon the other reaction conditions, there thereby result all theoretically possible substitution products, from monomethylolmelamine up to hexamethylolmelamine. The methylolmelamines are readily water-soluble. Therefore, from the initial suspension there arises, upon warming, a clear aqueous solution with a very low viscosity which is fundamentally desired for the infiltration. At 55° C., the viscosity is 7 to 10 mPas (measured with Epprecht Rheomat 15 of Contraves AG, Zürich).

Since, in the process according to the present invention, the fixed tissue sample is warmed in a mixture of formaldehyde, melamine and water, at the moment of the formation of the water-soluble methylolmelamines, the sample is infiltrated with these monomers which are present in statu nascendi. Since all original tissues possess reactive functional groups capable of condensation reactions, especially hydroxyl, carboxyl, amino, thiol, amide and ester groups and the like, the water-soluble monomeric methylolmelamines which have penetrated into the tissue are firmly held in the tissue, be it by condensation reactions, be it by van der Waals forces or the like. Surprisingly, the infiltration of the tissue with the monomeric methylolmelamines, obviously favoured by condensation reactions taking place within the tissue, appears to proceed more quickly than the competing polycondensation reaction of the monomeric methylolmelamines with one another. With an increasing degree of condensation, the polymeric methylolmelamine condensates become water-insoluble, which, after 2 to 2.5 hours warming of the mixture used according to the present invention, makes itself noticeable by a slight turbidity of the initially resulting clear solution. At this point of time, the water exchange in the tissue has already finished; therefore, the polycondensation of the monomeric methylolmelamines is no longer disturbing but rather, on the other hand, is desired. In the following drying of the tissue, infiltrated and subsequently embedded in casting resin, which take place according to known methods, it is completed up to complete hardening by three-dimensional cross-linking.

The tissue samples treated according to the present invention can be cut in an excellent manner, show no anisotropy for the electron beam passing therethrough but rather a high transparency and stability and they can be produced with optimum maintenance of structure of the biological material so that they also satisfy all histochemical requirements. In addition, for the expert in the field in question, it is completely surprising that, according to the present invention, the plastification of tissue with the help of a modified aminoplast is successful without embrittlement, i.e. without shrinkage of the resin during the polycondensation, although all previous attempts in this direction, especially with urea-formaldehyde polycondensates, have been completely unsatisfactory.

The present invention also provides a hardenable infiltration agent for biological tissue, especially for the preparation of tissue samples for thin layer electron microscopy, which comprises at least one monomeric, water-soluble methylolmelamine or an aqueous solution thereof and preferably consists of such monomeric methylolmelamines or of aqueous solutions thereof. However, the infiltration agent according to the present invention can, in addition to the monomeric methylolmelamines, optionally also contain known water-miscible resins or resin solutions, such as are described, for example, in the abovementioned publication, or also oligomeric or polymeric methylolmelamine condensates with a low degree of condensation, insofar as they are still miscible with water.

In the case of an advantageous embodiment of the process according to the present invention, the mixture in which the tissue sample is warmed contains formaldehyde and melamine in a mole ratio of 2:1 to 8:1 and preferably in a mole ratio of 6:1, in the case of which, in the first place, trimethylolmelamine and hexamethylolmelamine are formed, both of which are especially readily water-soluble and give rise to aqueous solutions with an especially low viscosity (less than 60 mPas at 25° C.).

The mixture containing the tissue sample is preferably warmed for at least one hour to a temperature of from 30° to 60° C. Excellent results have been achieved in the case of a warming and action period of 1 to 3 hours at a temperature of about 50° to 60° C.; at this temperature, the melamine dissolves at a mole ratio of 1:6 (melamine/formaldehyde) in about 20 minutes in a 37 to 40% aqueous formalin solution.

In the case of a further advantageous embodiment of the process according to the present invention, the mixture is adjusted to pH >7, preferably to a pH value of from 8 to 9, by the addition of an aqueous base, preferably 0.1N aqueous sodium hydroxide or potassium hydroxide solution. However, the process can also be carried out in neutral or acidic solution. For the adjustment of the pH value in the acidic range, use can be made of a dilute aqueous solution of an organic mono- or dibasic acid or also of a mineral acid.

After completion of the water exchange, i.e. after a warming time of about 1 to 3 hours, the infiltrated tissue sample is removed from the reaction mixture, transferred to a casting mould and embedded in any desired casting resin known for this purpose which is then dried in several stages in known manner, whereby not only the infiltration agent but also the casting resin used as embedding mass polymerise completely and harden by three-dimensional cross-linking. The multistage drying lasts for several days and usually commences in a desiccator which is provided with a non-volatile drying agent, such as silica gel or calcium chloride, at a temperature which lies only 10° to 15° C. above ambient temperature, drying then being continued at higher temperatures in a drying cabinet. Due to the water loss in the case of drying, the cast resin blocks first settle but the still not fully polymerised and still not cross-linked resin can still flow at this drying stage so that, in the case of the actual hardening, surprisingly no noteworthy shrinkage occurs.

According to the present invention, a melamine resin is preferably used as the casting resin. Especially preferably, there is thereby used an aqueous methylolmelamine ether solution which optionally also contains 10 to 20% by weight of polyethylene glycol with an average molecular weight of about 10,000 but which can also contain other known polyglycols or additions of other known casting resins. Especially preferable casting resins are the methylolmelamine methyl ethers and other lower alkyl ethers. Finally, from the dried, cross-linked, hardened cast resin blocks, which contain the tissue sample to be investigated, plastified by polycondensation and hardening of the infiltration agent, there are cut out, with a diamond cutter, at normal cutter angle and a cutting speed of 0.5 to 2 mm./s., ultrathin sections which are taken directly from the waterbath on to the fine copper meshes normally used for this purpose, which do not need to be coated with a thin protective foil, and examined electron microscopically.

The following examples are given for the purpose of illustrating the present invention:

EXAMPLE 1

Pieces of liver, hypophysis, retina and diaphragm muscle of the rat were fixed for 2 to 6 hours in an aqueous solution which contained 1% by weight glutaraldehyde and 1% by weight tannic acid, dissolved in 0.1M phosphate buffer (pH 7.2), the osmolarity of which had been adjusted with saccharose to 330 mosm. The fixed tissue samples were washed in double distilled water and, for contrasting, left for 24 hours at 40° C. in the dark in an aqueous 1% by weight uranyl acetate solution. Thereafter, the samples were again washed in double distilled water and subsequently placed in glass vessels with screw lids which contained a mixture of 0.01 mole melamine and 0.06 mole formaldehyde in the form of a 37% aqueous formalin solution which had been adjusted to a pH of 8.4 by means of 0.1M aqueous sodium hydroxide solution. The glass vessels were warmed for 2 hours in a waterbath to about 55° C., with continuous slow rotation. After about 20 minutes, from the initial suspension there had developed a clear aqueous solution. After about 2 hours, a slight turbidity was noticeable, which indicated the ending of the water exchange in the tissue samples and the increasing polymerisation or condensation of the monomeric methylolmelamines. The samples were then taken from the reaction solution and transferred to silicon casting moulds which were filled with a 50% aqueous solution of methylolmelamine ether resin which had been adjusted with phosphoric acid to pH 5 to 6 and which had previously been evacuated in order to avoid the formation of air bubbles. In the case of some of the samples, 10 to 20% by weight of polyethylene glycol with an average molecular weight of 10,000 had also been added to the casting resin solutions.

The hardening of the cast bodies took place by drying in three stages: First, drying was carried out in a desiccator (silica gel) for 2 days at 40° C., thereafter without desiccator in a drying cabinet at 60° C. for a further 2 days and finally for a further 4 hours in a drying cabinet at 80° C. Due to the water loss, the surfaces of the blocks in the casting moulds dropped but the hardening of the resin took place without shrinkage. Ultrathin sections were cut out from the hardened blocks with a diamond cutter.

The methylolmelamine ether solution used as casting resin was prepared as follows:

126 g. (1 mole) Melamine were mixed with 450 g. (6 mole) 40% formalin solution and the mixture was adjusted with 1N aqueous sodium hydroxide solution to pH 8.5 and heated to 80° C. The melamine hereby dissolved with the formation of hexamethylolmelamine. To the resultant hexamethylolmelamine solution was added a solution of 0.5 g. oxalic acid in 320 g. (10 mole) methanol and the whole was heated to the boil under reflux for 10 to 15 minutes, the hexamethylolmelamine thereby being partly etherified with methanol. Thereafter, the solution was again adjusted with 1N aqueous sodium hydroxide solution to pH 8.5 and concentrated under reduced pressure at a bath temperature of about 50° C. on a rotation evaporator until practically no more solvent passed over. The remaining slightly turbid solution was taken up in 400 ml. chloroform and left for 24 hours in a separating funnel. The residual water remaining in the residue separated out as an upper layer, whereas the greater part of the resin was present in the lower chloroform phase. The chloroform phase was separated off, the solvent was stripped off in a rotary evaporator, the residue was taken up in water and again kept in a rotary evaporator under reduced pressure until the solution was completely chloroform-free. The final solution was diluted with water to a resin content of 50% by weight. The clear solution was miscible with water in all proportions, was free from salts and was stable for many months at ambient temperature.

EXAMPLE 2

In a glass vessel with a screw lid, 1/100 mole melamine and 6/100 mole formaldehyde, in the form of a 37% solution of paraformaldehyde in water, was adjusted with 2% phosphoric acid to pH <7 and preferably to pH 5.5-6.5. After the addition of any desired tissue samples, these were infiltrated at 30° to 60° C. and preferably at 55° C., with slow rotation, the melamine thereby dissolving after 10 to 20 minutes, the whole procedure taking 1 hour. A turbidity of the solution must not occur. The samples were removed from the so obtained solution and transferred to silicon moulds. On to the samples there was, in each case, additionally applied one drop of about 25 $\mu$l. incubation solution which completely covered the pieces of tissue. Further treatment took place subsequently, without the use of a desiccator, in a warm cabinet for 24 hours at 60° C. Infiltration and hardening were thereafter completely concluded. The tissue sample was present as a small platelet surrounded by hardened melamine resin. For the better handling in the production of thin sections, this platelet (excess resin can previously be carefully separated off) was embedded in an epoxide resin or in any other appropriate available casting resin. This casting resin has no influence on the tissue sample, it serving exclusively for holding purposes. After trimming of the blocks, thin sections can be produced at a normal cutting angle with a diamond cutter or with a glass knife. With this embodiment of the process according to the present invention, satisfactory sections of tissue which is especially difficult to cut, such as of the brain, can also be produced satisfactorily in the simplest way.

The infiltration agent according to the present invention is preferably used in the form of a kit of a reagent batch which, in separate containers, contains stoichiometric amounts of melamine, formaldehyde and water so that the contents of the individual containers only need to be mixed together for the production of an infiltration or incubation solution. Especially advantageous is a reagent batch which, in separate containers, contains stoichiometric amounts of melamine and of a dilute aqueous formalin solution which optionally contains an agent for the adjustment of the pH value.

We claim:

1. In a process for the production of thin sections of biological tissue which includes dehydrating a fixed tissue sample to be investigated by infiltration of said fixed tissue sample with a hardenable medium miscible with water, subsequently embedding the dehydrated and infiltrated sample in a casting resin, and thereafter cutting thin sections from the cast body resulting from hardening of said casting resin, the improvement which comprises carrying out said infiltration by warming said fixed tissue sample in a mixture of formaldehyde, melamine and water, and during said warming said mixture forms water soluble monomeric methylolmelamines which infiltrate said tissue sample and undergo polycondensation to form water-insoluble polymeric methylolmelamine condensates in said tissue.

2. The improvement claimed in claim 1, wherein the mixture in which the tissue sample is warmed contains formaldehyde and melamine in a mole ratio of 2:1 to 8:1.

3. The improvement claimed in claim 2, wherein the mixture in which the tissue sample is warmed contains formaldehyde and melamine in a mole ratio of 6:1.

4. The improvement claimed in claim 1, wherein warming the mixture containing the tissue sample is by heating for at least one hour at a temperature of from 30° to 60° C.

5. The improvement claimed in claim 4, wherein the temperature is from 50° to 60° C.

6. The improvement claimed in claim 5, wherein the mixture is adjusted to a pH of greater than 7 by the addition of an aqueous base.

7. The improvement claimed in claim 6, wherein the mixture is adjusted to a pH of from 8 to 9.

8. The improvement claimed in claim 1, further including the casting resin in which the infiltrated tissue sample is embedded is a melamine resin.

9. The improvement claimed in claim 8, wherein an aqueous methylolmelamine ether solution is used for embedding in the melamine resin.

10. The improvement claimed in claim 9, wherein the aqueous methylolmelamine ether solution additionally contains 10-20% by weight of polyethylene glycol.

* * * * *